United States Patent [19]

Mullane, Jr.

[11] Patent Number: 4,509,908

[45] Date of Patent: Apr. 9, 1985

[54] APPARATUS FOR UNIFORMLY DEBOSSING AND APERTURING A RESILIENT PLASTIC WEB

[75] Inventor: William I. Mullane, Jr., Cincinnati, Ohio

[73] Assignee: The Procter & Gamble Company, Cincinnati, Ohio

[21] Appl. No.: 519,614

[22] Filed: Aug. 2, 1983

Related U.S. Application Data

[62] Division of Ser. No. 230,488, Feb. 2, 1981, Pat. No. 4,441,952.

[51] Int. Cl.³ .............................................. B29C 17/04
[52] U.S. Cl. .................................. 425/290; 264/504; 425/387.1; 425/388
[58] Field of Search ...................... 425/290, 388, 326.1, 425/387.1; 264/504, 555, 556, 154, 156

[56] References Cited

U.S. PATENT DOCUMENTS

| Re. 23,910 | 12/1954 | Smith et al. |  |
|---|---|---|---|
| Re. 29,524 | 1/1978 | Spencer | 428/134 |
| 691,804 | 1/1902 | Parker . |  |
| 2,166,366 | 7/1939 | Norris . |  |
| 2,776,451 | 1/1957 | Chavannes . |  |
| 2,809,392 | 10/1957 | Armstrong . |  |
| 2,816,025 | 12/1957 | Dahlberg . |  |
| 2,820,985 | 1/1958 | Cresswell . |  |
| 2,857,657 | 10/1958 | Wheeler, Jr. | 29/156.8 |
| 2,926,490 | 3/1960 | Eaton et al. . |  |
| 3,054,148 | 9/1962 | Zimmerli . |  |
| 3,123,446 | 3/1964 | Wheeler, Jr. . |  |
| 3,174,837 | 3/1965 | Mears . |  |
| 3,390,447 | 7/1968 | Mears . |  |
| 3,560,601 | 2/1971 | Johnson et al. | 264/93 |
| 3,814,101 | 6/1974 | Kozak | 128/287 |
| 3,844,027 | 10/1974 | Hagen et al. . |  |
| 3,929,135 | 12/1975 | Thompson | 128/287 |
| 3,957,414 | 5/1976 | Bussey, Jr. et al. | 264/504 |
| 3,979,494 | 9/1976 | Ericson | 156/252 |
| 3,989,867 | 11/1976 | Sisson | 428/132 |
| 4,038,040 | 7/1977 | Nagl | 428/596 |
| 4,041,951 | 8/1977 | Sanford | 128/287 |
| 4,151,240 | 4/1979 | Lucas et al. | 264/504 |
| 4,248,822 | 3/1981 | Schmidt | 264/154 |
| 4,342,314 | 8/1982 | Radel et al. | 128/287 |

FOREIGN PATENT DOCUMENTS

| 1300449 | 6/1972 | France | 428/137 |
|---|---|---|---|
| 48-18940 | 6/1973 | Japan | 156/253 |
| 2014508 | 8/1979 | United Kingdom . |  |
| 2014903 | 9/1979 | United Kingdom . |  |

*Primary Examiner*—Jan Silbaugh
*Attorney, Agent, or Firm*—Richard C. Witte; E. Kelly Linman; Ronald J. Snyder

[57] ABSTRACT

Method and apparatus for imparting a uniformly apertured three-dimensional pattern to a heated plastic material subjected to a fluid pressure differential while in contact with said forming structure. In a preferred embodiment, said forming structure is created by forming a substantially continuous pattern of apertures in a multiplicity of planar sheets, at least a portion of said sheets having aperture patterns which are concentrically aligned but dissimilar in size to one another. The sheets having said concentrically aligned aperture patterns are thereafter superposed upon one another so as to form a stack exhibiting a three-dimensional continuum of capillary networks. A sufficient number of laminae are employed to ensure that said networks are of greater overall length than the maximum depth to which the plastic film being processed thereon is drawn when subjected to said fluid pressure differential. Said capillary networks exhibit a cross sectional area which reaches a minimum intermediate the uppermost and lowermost surfaces of the stack and thereafter increases in the direction of the lowermost surface of the stack to increase fluid permeability. The superposed sheets are bonded to one another at contact points while in the stacked configuration to form an integral laminate structure. The laminate forming structure is preferably caused to assume a tubular shape and its opposing free edges are secured to one another without disrupting the three-dimensional continuum of capillary networks along its periphery, thereby facilitating continuous plastic web processing against its outermost surface. The tubular laminate forming structure is preferably supported on a cylindrical drum by a multiplicity of radially oriented support members having lands which contact the innermost surface of the tubular member, but which are of insufficient cross-section to obstruct fluid flow through the capillary networks.

13 Claims, 14 Drawing Figures

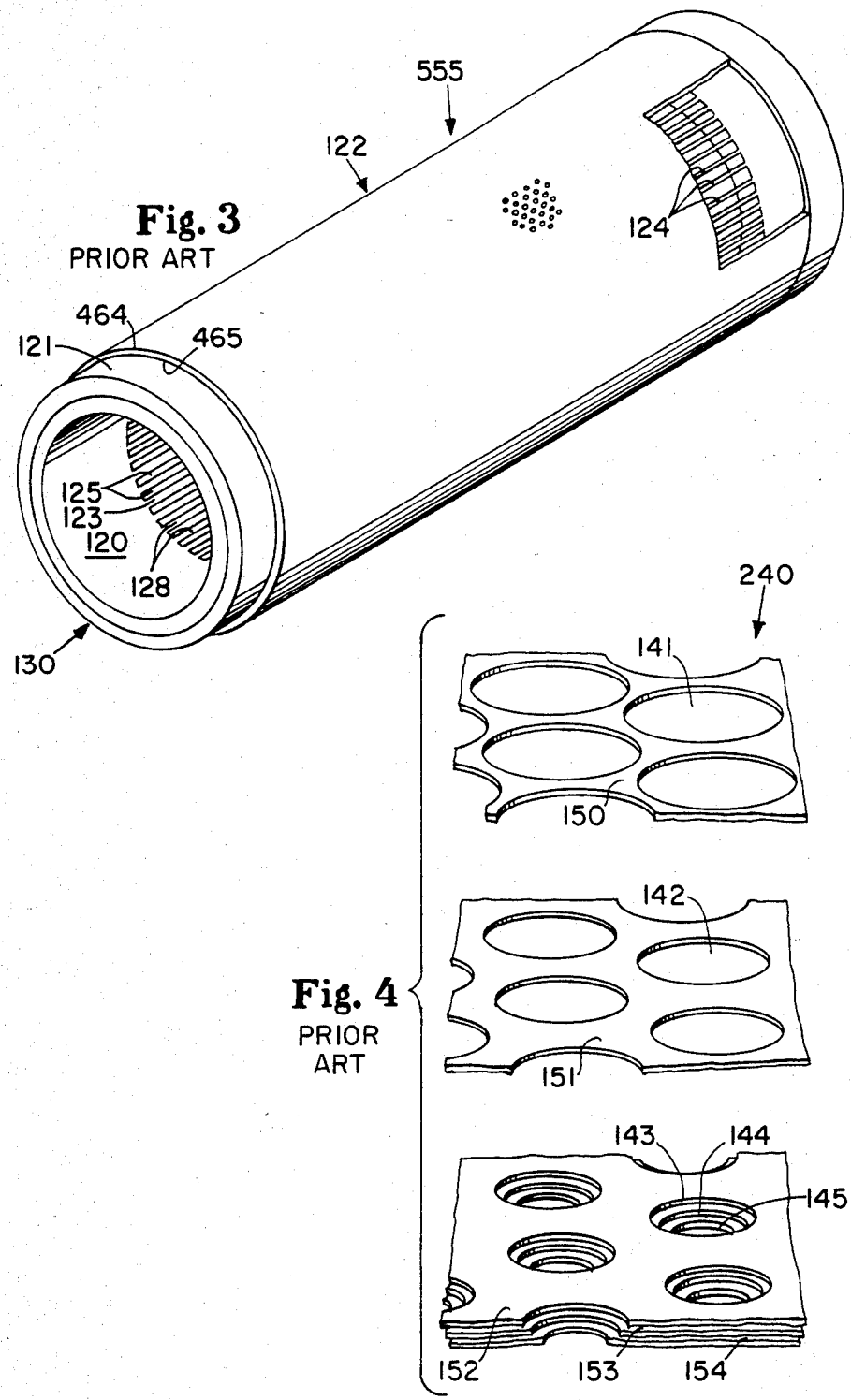

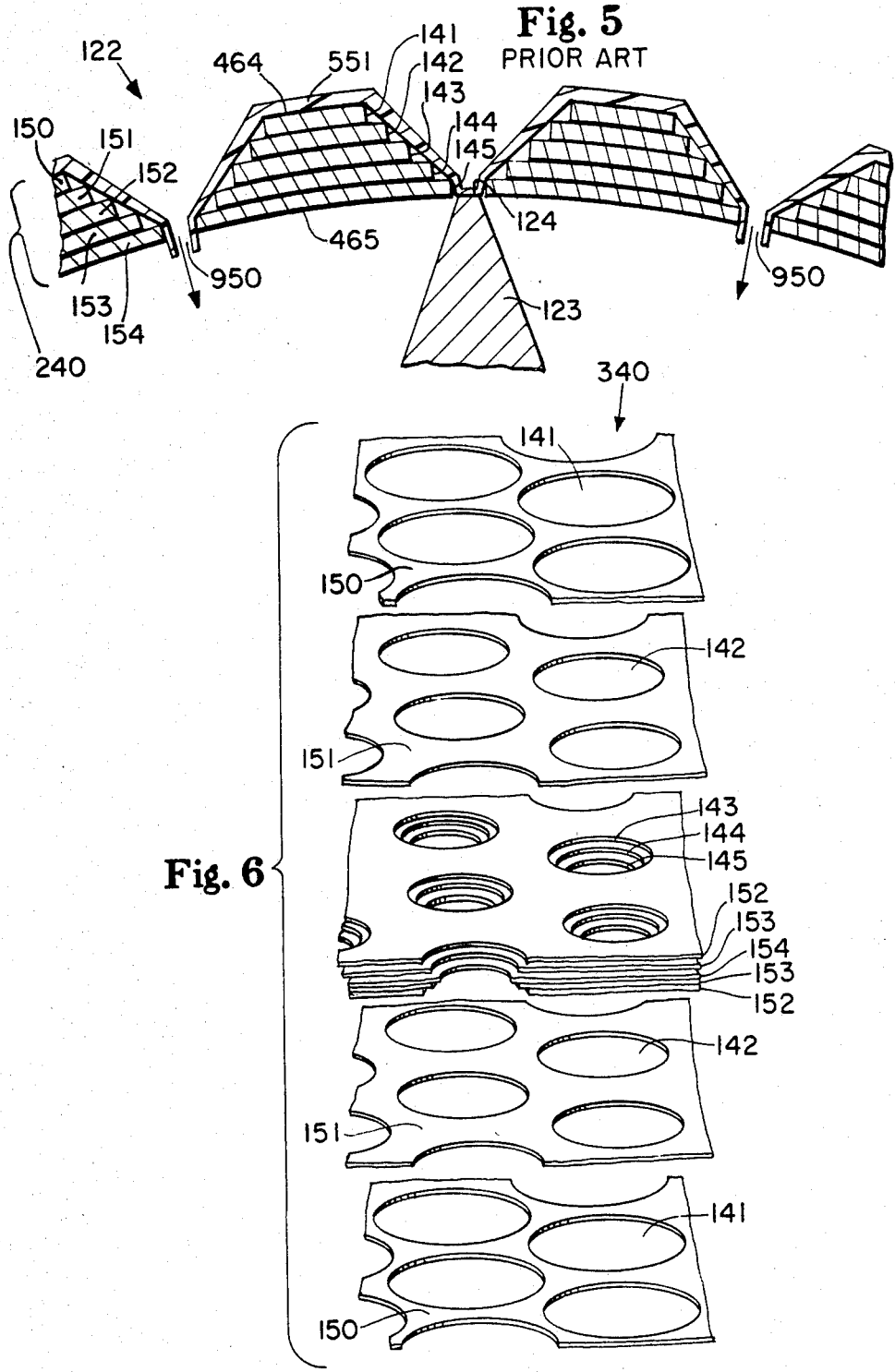

APPARATUS FOR UNIFORMLY DEBOSSING AND APERTURING A RESILIENT PLASTIC WEB

This is a division of application Ser. No. 230,488, filed Feb. 2, 1981 now U.S. Pat. No. 4,441,952.

TECHNICAL FIELD

The present invention has relation to uniformly apertured, resilient plastic webs exhibiting fine-scale three-dimensional characteristics.

The present invention has further relation to method and apparatus for vacuum forming said plastic webs by providing a forming structure which is uniformly pervious to fluid flow in the areas where aperturing of the film is desired.

The present invention has still further relation to a method for constructing film forming structures suitable for debossing and uniformly aperturing said plastic webs throughout the entire area where aperturing is desired.

Means for debossing and aperturing plastic webs are known in the art. Commonly assigned U.S. Pat. No. 4,151,240 issued to Lucas et al. on Apr. 24, 1979 discloses a particularly preferred method and apparatus for debossing and perforating a running ribbon of thermoplastic film, said patent being hereby incorporated herein by reference. Briefly, the apparatus disclosed in the Lucas et al. patent comprises means for continuously converting a ribbon of thermoplastic film into a debossed and perforated film by directing hot air jets against one surface of the film while applying vacuum adjacent the opposite surface of the film. The aforementioned operations are carried out while maintaining sufficient control of the film to substantially obviate wrinkling and/or macroscropically distending the film. In a particularly preferred embodiment, the debossing and perforating means include a rotatably mounted debossing/perforating cylinder having closed ends, a nonrotating triplex vacuum manifold assembly and hot air jet means. The filmcontacting surface of the debossing/perforating cylinder exhibits the pattern to be imparted to the plastic film to be treated thereon.

In a particularly preferred embodiment of the Lucas et al. invention, the debossing/perforating cylinder is constructed employing a laminate forming structure of the type generally described in the commonly assigned patent application of Clifford Radel and Hugh A. Thompson, Ser. No. 206,410, filed Nov. 13, 1980 and entitled RESILIENT PLASTIC WEB EXHIBITING FIBER-LIKE PROPERTIES AND METHOD AND APPARATUS FOR ITS MANUFACTURE, said patent application being issued as U.S. Pat. No. 4,342,314 on Aug. 3, 1982 and hereby incorporated herein by reference. Forming structures of this type permit the production of apertured three-dimensional plastic webs having a predetermined, precisely regulated pattern of such fine scale as to appear fiber-like to the naked eye.

In order to provide fluid permeability, plastic webs produced in accordance with the teachings of the aforementioned application of Radel et al. may be provided with a pattern of closely-spaced fine scale capillary networks. Where improved fluid transport from the uppermost to the lowermost surface of the web is desired, said capillary networks preferably exhibit a decreasing cross-section from the uppermost to the lowermost surface of the web. However, such decreasing cross-section capillary networks reduce even further the size of the apertures whih must be provided in the forming structure employed to produce such webs. Accordingly, when forming structures of the type disclosed in the aforementioned Radel et al. application (which issued as U.S. Pat. No. 4,342,314 on Aug. 3, 1982) are utilized to construct a debossing/perforating drum generally in accordance with the teachings of the patent to Lucas et al., the support members utilized to reinforce the tubular shaped laminate forming structure are likely to obstruct or totally block the fluid permeability of the forming structure at points of contact therebetween. This reduces the effectiveness of the vacuum applied to the interior surfaces of said drum at said points of contact. Furthermore, the forming structure support members may actually contact and provide support to the film being processed, thereby tending to prevent rupture thereof at such points. As a result, finely apertured films produced utilizing this technique are typically not apertured wherever such a support member contacts the lowermost, i.e., the innermost, surface of the tubular shaped forming structure, particularly in situations where the overall thickness of the laminate forming structure is relatively thin. This is undesirable from both an aesthetic standpoint as well as from a functional standpoint in those situations where uniform film permeability is desired.

Accordingly, it is an object of the present invention to provide a three-dimensional plastic film exhibiting a fine scale pattern of uniformly apertured capillary networks throughout those areas where fluid permeability is desired.

It is another object of the present invention to provide continuous method and apparatus for debossing and uniformly perforating a heated plastic web in nearly any desired pattern by subjecting the entire surface of said web to a uniform fluid pressure differential on a forming structure of the present invention.

It is another object of the present invention to provide such method and apparatus which is equally compatible with systems designed to process a web fed from a roll of unprocessed plastic film and systems designed to extrude a molten plastic material directly onto the surface of the forming structure.

It is yet another object of the present invention to provide methods for constructing three-dimensional forming structures for imparting a uniformly apertured, fine scale three-dimensional pattern to a heated plastic web which is subjected to a fluid pressure differential while in contact therewith.

DISCLOSURE OF THE PRESENT INVENTION

The present invention pertains, in a particularly preferred embodiment, to the provision of a three-dimensional resilient plastic web exhibiting a fine scale uniformly apertured appearance throughout those areas where fluid permeability is desired, as well as to method and apparatus for producing such a web. The uniformity of aperturing is controlled by the character of the forming surface on which the plastic material comprising the web is subjected to a fluid pressure differential.

In yet another preferred embodiment of the present invention, a method for constructing a three-dimensional film forming structure for imparting such a uniformly apertured three-dimensional pattern to either a heated plastic film or a heated plastic melt subjected to a fluid pressure differential while in contact with its surface is provided. Said method preferably comprises the steps of:

(1) forming substantially continuous patterns of apertures in a multiplicity of planar sheets, at least a portion of said sheets having aperture patterns in which the apertures at least to a degree coincide from one sheet to another, at least a portion of said coinciding apertures being dissimilar in size from one lamina to another;

(2) superposing said sheets having said patterns of coinciding, dissimilarly sized apertures upon one another so as to form a stack exhibiting a fine scale, three-dimensional continuum of capillary networks, said networks having an overall length greater than the maximum depth to which the plastic film being processed thereon is drawn when subjected to said fluid pressure differential and a cross-sectional area which increases from the minimum cross-sectional area present intermediate the uppermost and lowermost surfaces of the stack in the direction of the lowermost surface of said stack;

(3) bonding said superposed sheets to one another at contact points while in the stacked configuration to form an integral laminate structure;

(4) causing the uppermost surface of said laminate structure to assume a radius of curvature greater than that of said lowermost surface of said laminate structure without causing delamination thereof, thereby causing said laminate structure to assume a substantially tubular shape; and (5) securing the opposing free edges of said tubular shaped laminate structure to one another while maintaining substantial continuity of said three-dimensional continuum of capillary networks about the entire periphery of the tubular member thus formed.

The innermost surface of said tubular laminate structure is preferably supported on a cylindrical cage having a multiplicity of support members, each having a thickness, as measured in the direction of web travel, which is insufficient to block the capillary networks present in the laminate structure at the points of contact between the innermost surface of the laminate structure and said support members. The inability of the support members to block said capillary networks ensures substantially uniform fluid permeability about the periphery of the drum, while the additional lamina employed to increase the cross-sectional area of the capillary networks in the direction of the innermost surface of the drum increases the overall thickness of the laminate forming structure. Substantially uniform permeability of the forming structure ensures that all surfaces of the film are subjected to a uniform level of suction, while the increased thickness of the forming structure prevents the plastic film from contacting and being reinforced by the support members during processing.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

FIG. 3 is an enlarged perspective view of the debossing/aperturing cylinder shown in FIGS. 1 and 2;

FIG. 4 is an enlarged, partially exploded segment of a laminate film forming structure (shown prior to rolling and seaming) of the type generally disclosed in the commonly assigned patent application of Clifford Radel and Hugh A. Thompson, Ser No. 206,410, filed Nov. 13, 1980, issued as U.S. Pat. No. 4,342,314 on Aug. 3, 1982, and entitled RESILIENT PLASTIC WEB EXHIBITING FIBER-LIKE PROPERTIES AND METHOD AND APPARATUS FOR ITS MANUFACTURE, said structure being comprised of a multiplicity of planar sheets having a pattern of concentrically aligned holes of decreasing diameter superposed upon one another;

FIG. 5 is an enlarged, simplified cross-sectional segment of a tubular forming structure formed from a laminate of the type generally shown in FIG. 4 installed on a cylindrical cage of the type generally shown in FIGS. 1-3;

FIG. 6 is an enlarged, partially exploded segment of a laminate forming structure (shown prior to rolling and seaming) of the present invention;

DETAILED DESCRIPTION OF THE PRESENT INVENTION

Figure 1:
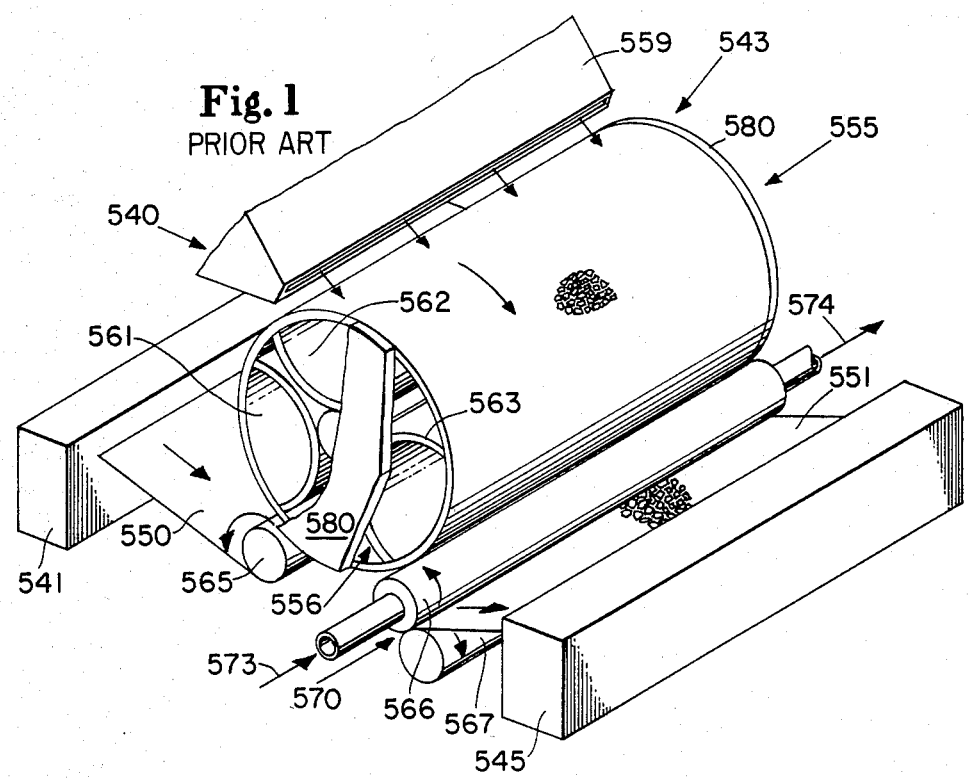
FIG. 1 is a simplified schematic illustration of a preferred method and apparatus for debossing and uniformly aperturing a plastic film generally in accordance with the present invention.

A particularly preferred continuous film forming process which may employ a tubular forming structure of the present invention is schematically illustrated in FIG. 1. This process is generally described in commonly assigned U.S. Pat. No. 4,151,240 issued to Malcolm B. Lucas and Robert H. Van Coney on Apr. 24, 1979, said patent being incorporated herein by reference. The particularly preferred apparatus 540 shown in FIG. 1 includes constant tension film supply means 541, debossing and perforating means 543, and constant tension film forwarding and winding means 545. The frame, bearings, supports and the like which must necessarily be provided with respect to the functional members of apparatus 540 are not shown or described in detail in order to simplify and more clearly depict and disclose the present invention, it being understood that such details would be obvious to persons of ordinary skill in the art of designing plastic film converting machinery.

Briefly, apparatus 540, FIG. 1, comprises means for continuously converting a planar ribbon of thermoplastic film 550 into a three-dimensional debossed and perforated or apertured film 551 by directing hot air jets against one surface of the film while applying vacuum adjacent the opposite surface of the film, and while maintaining sufficient control of the film to substantially obviate wrinkling and/or macroscopically distending the film. Thus, as will be more fully described hereinafter, the apparatus 540 comprises means for maintaining constant machine direction tension in the film both upstream and downstream of a zone where the temperature is greater than the thermoplastic temperature of the film, but in which zone there is substantially zero machine direction and cross-machine direction tension tending to macroscopically distend the film. The aforementioned upstream and downstream tension is required to control and smooth the running ribbon of thermoplastic film. The zero tension zone results from the film in the zone being at a sufficiently high temperature to enable debossing and uniformly perforating or aperturing it through the use of heat and vacuum. The perforations shown in FIG. 1 are greatly enlarged to enable visually perceiving the nature of the difference between the imperforate planar film 550 and the resulting three-dimensional debossed and perforated film 551, as more fully described hereinafter.

As utilized herein, the term "planar", when used to describe plastic ribbons and films, refers to the overall condition of the ribbon or film when viewed on a macroscopic scale. In this context "planar" ribbons and films may include ribbons having fine scale surface aberrations on one or both sides.

As can be seen in FIG. 1, the debossing and perforating means 543 includes a rotatably mounted debossing/perforating cylinder 555 having closed ends 580, a nonrotating triplex vacuum manifold assembly 556 and hot air jet means 559. The triplex vacuum manifold assembly 556 comprises three mainfolds designated 561, 562 and 563. Also shown in FIG. 1 is a freely rotatable lead-on idler roll 565, a power rotated lead-off/chill roll 566, and a soft-faced (e.g., low density neoprene) roll 567 which is driven with the chill roll.

Briefly, by providing means (not shown) for independently controlling the degree of vacuum in the three vacuum manifolds, a thermoplastic ribbon of film running circumferentially about a portion of debossing/perforating cylinder 555 is sequentially subjected to a first level of vacuum by manifold 561, a second level of vacuum by manifold 562, and a third level of vacuum by manifold 563. As will be described more fully hereinafter, vacuum applied to the film by manifold 561 enables maintaining upstream tension in the film, vacuum applied by manifold 562 enables three-dimensionally debossing and perforating the film when hot air is directed radially inwardly against the film, and vacuum applied by manifold 563 cools the film to below its thermoplastic temperature and enables establishing downstream tension therein. If desired, the film contacting surface of the debossing/perforating cylinder 555 may be preheated prior to reaching vacuum manifold 562 by means well known in the art (and therefore not shown) to facilitate better conformance of plastic films comprised of flow-resistant polymers to the forming structure during the debossing and perforating operation. The nip 570 intermediate chill roll 566 and the soft-faced roll 567 is only nominally loaded to avoid ironing out the three-dimensional debossments which are formed in the film in the aforementioned manner. However, even nominal pressure in nip 570 helps the vacuum applied by manifold 563 to isolate downstream tension (i.e., roll winding tension) from the debossing/perforating portion of the debossing/perforating cylinder 555, and enables the nip 570 to peel the three-dimensionally debossed and perforated film from the debossing/perforating cylinder 555. Moreover, while ambient air passing through the film as it is drawn by vacuum into manifold 563 will normally cool the film to below its thermoplastic temperature, the passage of coolant through the chill roll as indicated by arrows 573, 574 in FIG. 1 will enable the apparatus to handle thicker films or to be operated at higher speeds.

To summarize, the first vacuum manifold 561, and the third vacuum manifold 563 located within the debossing/perforating cylinder 555 enable maintaining substantially constant upstream and downstream tension, respectively, in a running ribbon of film while the intermediate portion of the film adjacent the second vacuum manifold 562 within the debossing/perforating cylinder 555 is subjected to tension vitiating heat and vacuum to effect three-dimensional debossing and perforating of the film.

Referring again to FIG. 1, the constant tension film supply means 541 and the constant tension film forwarding and winding means 545 may, if desired, be substantially identical to and function substantially identically to the corresponding portions of the apparatus shown and described in commonly assigned U.S. Pat. No. 3,674,221 issued to Reimersma on July 4, 1972 and which is hereby incorporated herein by reference. The debossing and perforating means 543 comprises the rotatably mounted debossing/perforating cylinder 555, means (not shown) for rotating the cylinder 555 at a controlled peripheral velocity, the non-rotating triplex vacuum manifold assembly 556 inside the debossing/perforating cylinder 555, means (not shown) for applying controlled levels of vacuum inside the three vacuum manifolds 561, 562, and 563 comprising the triplex manifold assembly 556, and hot air jet means 559.

The debossing/perforating cylinder 555 may be constructed by generally following the teachings of the aforementioned commonly assigned patent of Malcolm B. Lucas and Robert H. Van Coney, but substituting a film-contacting tubular forming structure of the present invention for the perforated tubular forming structure disclosed therein.

Figure 2:
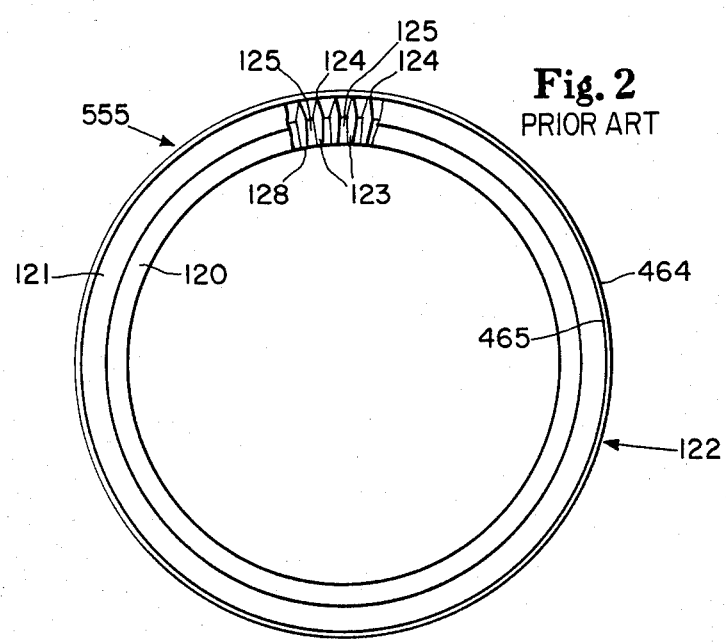
FIG. 2 is an enlarged end view of the debossing/aperturing cylinder shown in FIG. 1.

The debossing/perforating cylinder 555 shown in FIG. 1 is illustrated in greater detail in FIGS. 2 and 3. The cylinder 555 comprises a cage 120, a support ring 121 and a relatively thin walled film-contacting tubular member 122. The cage 120 comprises a multiplicity of circumferentially spaced, longitudinally extending bars 123 which are tapered to relatively small, radially outwardly facing lands 124. The spaced bars 123 have vacuum communicating passageways 125 provided therebetween. The bars 123 also have radially inwardly facing lands 128 which corporately provide a cylindrical vacuum sealing surface against which the vacuum seals associated with the triplex vacuum manifold 556 are biased. Thus, as the debossing/perforating cylinder 555 rotates, its vacuum sealing surface slides over the seals (not shown) of the non-rotating triplex vacuum manifold assembly 556.

The end 130, FIG. 3, of the debossing/perforating cylinder 555 disposed remotely from its driven end is open in order to provide easy insertion/removal of the triplex vacuum manifold assembly 556. Therefore, in order to rotatably support the open end 130 of cylinder 555, it is provided with a bearing-race support ring 121, as shown in FIGS. 2 and 3, which rides on bearings (not shown) which are appropriately secured to the apparatus frame (not shown).

Tubular member 122 is fluid pervious and may comprise a relatively thin laminate structure such as 240, a partially exploded planar segment of which is shown in FIG. 4, in contacting relation with the small lands 124 of the longitudinally extending support bars 123 of cage 120. The lands 124 are small and the tubular member 122 is relatively thin-walled because the preferred embodiment apparatus 540, FIG. 1, is configured to deboss and perforate an extremely fine three-dimensional, apertured pattern into a relatively thin thermoplastic film such as low density polyethylene film, as will be described in greater detail hereinafter.

The tubular member 122 shown in FIGS. 1–3 may be constructed generally in accordance with the teachings of the, commonly assigned patent application of Clifford Radel and Hugh A. Thompson, Ser. No. 206,410, filed Nov. 13, 1980, issued as U.S. Pat. No. 4,342,314 on Aug. 3, 1982, and entitled RESILIENT PLASTIC WEB EXHIBITING FIBER-LIKE PROPERTIES AND METHOD AND APPARATUS FOR ITS MANUFACTURE, said patent application being hereby incorporated herein by reference.

Only the outermost surface 464 of the tubular forming member 122 contacts the plastic webs brought in contact therewith. The innermost surface 465 of the tubular member contacts the lands 124 of support members 123 during the debossing/perforating operation.

In the illustrated embodiment, the tubular member 122 is constructed generally in accordance with the teachings of the aforementioned application of Radel and Thompson (which issued as U.S. Pat. No. 4,342,314) utilizing a stack of copper plated, photo-etched metallic lamina exhibiting concentrically aligned patterns of apertures, said lamina being bonded to one another at contact points while subjected to heat and pressure. The resultant laminate structure is thereafter rolled into a tubular shape and its free edges are bonded to one another to form a continuous tubular forming structure in accordance with the teachings of the aforementioned application of Radel and Thompson (which issued as U.S. Pat. No. 4,342,314).

FIG. 4 is a simplified embodiment of a particular laminate structure 240 which could, if desired, be utilized to provide a surface suitable for debossing and perforating an initially imperforate, substantially planar plastic film to produce a fluid-pervious web exhibiting a fine scale pattern of tapered capillaries, as generally illustrated and described in U.S. Pat. No. 3,929,135 issued to Thompson on Dec. 30, 1975 and hereby incorporated herein by reference. The laminate structure 240 (shown prior to rolling and seaming) is comprised of a stack of individual lamina 151, 152, 153 and 154. Each lamina has a pattern of regularly spaced openings or apertures therein. In the illustrated embodiment, the pattern of openings 141 in lamina 150 is concentrically aligned with the pattern of openings 142 in lamina 151, the pattern of openings 143 in lamina 152, the pattern of openings 144 in lamina 153 and the pattern of openings 145 in lamina 154. Thus, the apertures in successive lamina coincide with one another. The diameter of openings 141 is greater than the diameter of openings 142 which in turn, is greater than the diameter of openings 143, etc., all the way through laminae 153 and 154. Thus, the resultant laminate structure 240 provides a regulated pattern of substantially conically-shaped openings extending from the uppermost lamina 150 to the lowermost lamina 154.

FIG. 5 is a greatly enlarged, simplified cross-sectional view of a segment of a tubular member 122 installed on a cylindrical cage 120 of the type shown in FIGS. 1–3, said tubular member being comprised of a tubular shaped rolled and seamed laminate structure 240 of the type generally shown in FIG. 4. FIG. 5 is taken during the film processing operation through a partially obstructed, conically-shaped capillary network created in laminate forming structure 240 by the concentrically aligned holes in each lamina. As shown in FIG. 5, the width of land 124 of support member 123 is such that it partially obstructs cylindrical opening 145 in lowermost lamina 154 of the laminate structure 240. As a result, when the plastic web is subjected to heat, in this case hor air blast 559, and vacuum is applied to the interior surface of debossing/perforating cylinder 555, the initially planar plastic film is caused to conform approximately to the tapered capillary networks generally illustrated in FIG. 5. However, as the film draws nearer the innermost surface 465 of tubular member 122, it contacts land 124 of support member 123. Thus, although the film is thinned due to its being forced to conform to the conically-shaped capillary network in the laminate structure 240, it is not perforated at this particular point due to the partial obstruction of air flow as well as the structural support imparted to the film by land 124 on support member 123 during processing. By way of contrast, the adjacent capillary networks in the laminate structure are unobstructed. Consequently, the film is both debossed and perforated at the unobstructed locations, as generally shown in FIG. 5, to form apertures 950 in the film 551.

Since the radially oriented support members 123 extend generally parallel to the cylinder's axis of rotation, the macroscopic effect of the obstruction illustrated in FIG. 5 is a continuous line of debossed, but imperforate film extending throughout the areas where support members 123 contact the innermost surface 465 of tubular member 122 and partially obstruct apertures 145 in lowermost lamina 154. Since a multiplicity of support members 123 is normally required to mechanically support tubular member 122 across the surface of the cylinder 555 about its entire periphery, a corresponding multiplicity of imperforate areas results in the film. While in the illustrated embodiments, these imperforate areas extend in a direction generally parallel to the cylinder's axis of rotation, it will be appreciated that the particular configuration and orientation of any imperforate areas exhibited by the web will be dependent upon the configuration and orientation of the particular support members employed to mechanically support tubular member 122.

In this regard it should be noted that not all apertured webs either processed from rolls of planar plastic film or extruded as a melt directly onto the surface of a forming structure will exhibit the imperforate characteristic described in the preceding paragraph. Where the apertures are large in relation to the area of obstruction created by land areas 124 of support members 123, the obstruction to fluid flow may prove insignificant. Complete aperturing may occur despite the presence of the obstruction to fluid flow, provided a second criteria is also met, namely a sufficient overall thickness of the forming structure. In situations where the overall thickness of a forming structure exhibiting substantially uniform fluid permeability is sufficient that rupturing of the film occurs before it can contact the land areas 124 of support members 123, the resultant plastic web will exhibit substantial uniformity of aperturing. It must be noted, however, that the maximum depth to which plastic films are drawn during processing is normally greater than the maximum thickness exhibited by the resultant debossed and apertured film. This is due to the elastic nature of plastic materials in general, which causes them to undergo a degree of retraction after being stretched. Since the elastic characteristics of different plastics vary greatly, the required overall thickness for a forming structure of the present invention to be used with a particular plastic material must take the elastic characteristics for said material into consideration.

From the foregoing explanation it is clear that practice of the present invention would yield a readily perceivable benefit in those situations where land areas 124 of support members 123 either significantly reduce the fluid permeability of the forming structure and/or contact and support the film being processed thereon prior to rupture thereof.

FIG. 6 is an illustration generally similar to that of FIG. 4, but showing a particularly preferred embodiment of a laminate forming structure 340 (shown prior to rolling and seaming) of the present invention. The structure of FIG. 6 differs from that illustrated in FIG. 4 in that the number of laminae has been increased to totally eliminate the support provided to the film by lands 124 on longitudinally extending support members 123. Furthermore, the order in which the laminae are stacked has been modified to maximize air flow during the film perforating operation. In the disclosed embodiment, another set of laminae 153, 152, 151, and 150 has been added to the lowermost surface of lamina 154. However, the added laminae are stacked in reverse order, as generally shown in FIG. 6, so that the resultant capillary networks connecting the outermost and innermost surfaces of tubular member 122', FIG. 7, first converge to a minimum cross-sectional area at lamina 154 and then diverge to their original cross sectional area from the outermost to the innermost surface of the tubular member.

Figure 7:
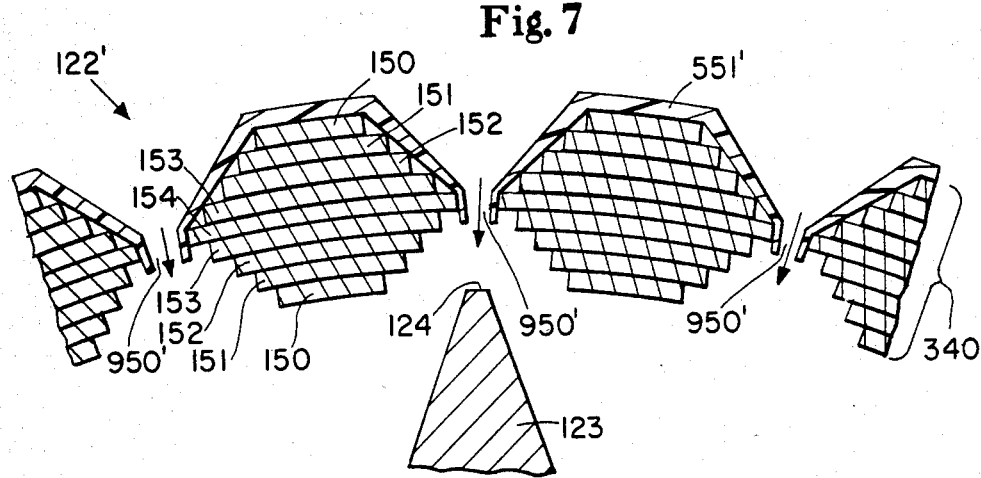
FIG. 7 is an enlarged, simplified cross-sectional segment of a tubular forming structure formed from a laminate of the type generally shown in FIG. 6 applied to a cylindrical cage of the type generally shown in FIGS. 1-3.

The effect of this structural difference is illustrated in simplified form in FIG. 7. Because the overall thickness of the tubular member 122' has been increased, the land areas 124 of longitudinally extending support members 123 are far enough removed from the surface of the plastic film being debossed and perforated that the film does not contact the support members during the perforating operation. Furthermore, because the lands 124 are considerably smaller in width than the diameter of the cylindrical apertures 141 in layer 150 adjacent thereto, fluid flow, in this case air, is not obstructed at the centrally located cylindrical openings 145 in lamina 154. As a result, the plastic film is drawn down into the cylindrical openings 145 contained in lamina 154, and, due to the lack of support, ruptures to form a uniform pattern of apertures 950' in film 551', as generally shown in FIG. 7.

Figure 8:
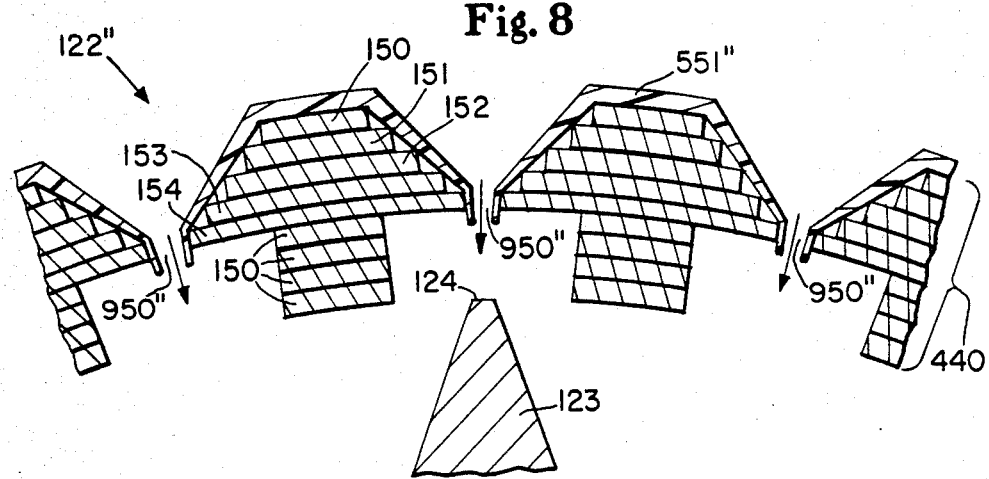
FIG. 8 is an enlarged, simplified cross-sectional segment similar to that of FIG. 7, but showing an alternative embodiment of a laminate forming structure of the present invention.

An alternative embodiment of a tubular member 122" of the present invention is comprised of a laminate forming structure 440 illustrated in FIG. 8, wherein all lamina 150 located beneath lamina 154 are provided with crylindrical apertures having a diameter substantially equal to that of apertures 141 in uppermost lamina 150. As with the embodiment disclosed in FIG. 7, the plastic film 551" is uniformly debossed and perforated to form an uninterrupted pattern of apertures 950" therein.

As will be understood by those skilled in the art, the present invention may be practiced to maximum advantage by minimizing the thickness of the land areas 124 as measured in the direction of web processing, and maximizing the size of the apertures in the lamina which contacts said land areas. However, it must be recognized that limiting cases exist where the capillary networks to be provided in the forming structure are so small in cross-section and so closely spaced to one another that the land areas 124 of the support members 123 cannot be made thin enough and the apertures in the lamina which contacts said land areas cannot be made large enough to substantially eliminate the resulting obstruction to fluid flow at the points of contact therebetween.

Figure 9:
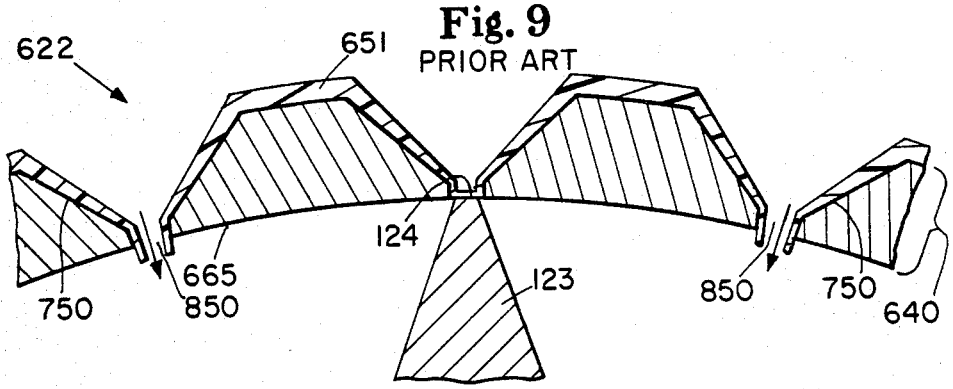
FIG. 9 is an enlarged, simplified cross-sectional segment of a single layer forming structure of the type generally disclosed in commonly assigned U.S. Pat. No. 4,151,240 issued to Lucas et al. applied to a cylindrical cage of the type generally shown in FIGS. 1-3.
Figure 13:
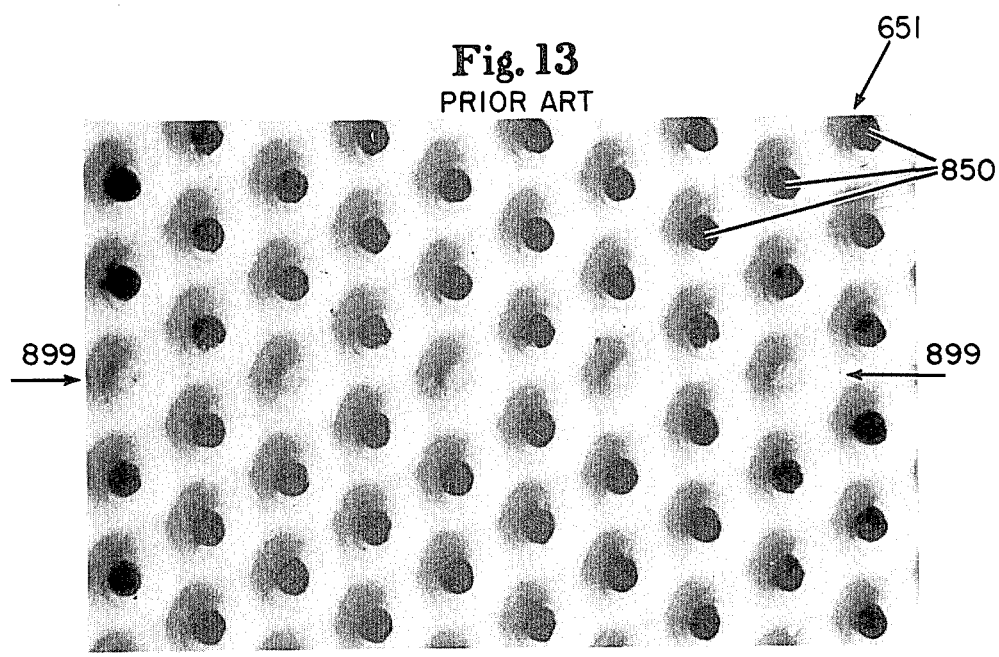
FIG. 13 is a further enlarged plan view photograph of the same film shown in FIG. 11, said film being shown approximately sixteen times actual size.

FIG. 9 is a simplified cross-sectional segment of a single layer tubular member 622 of the type generally disclosed in the aforementioned patent to Lucas et al. employed as the film-contacting surface on a debossing/perforating cylinder 555 of the type generally illustrated in FIGS. 1-3. In particular, the land areas 124 of longitudinally extending support members 123 are located immediately adjacent the innermost surface 665 of the single thickness layer 640 of which tubular forming member 622 is comprised. As with the embodiment generally disclosed in FIG. 5, portions of the plastic film 651 drawn into the tapered cylindrical capillary networks 750 in layer 640 contact the lands 124 of support members 123. As a result, the film 651 is not ruptured at these points of contact during the processing operation. The areas of contact between the film and support members 123 are clearly apparent from FIG. 11 (see arrows 899) which is a plan view photograph enlarged approximately seven times actual size of a plastic web 651 debossed and perforated on a single layer forming structure of the type generally illustrated in FIG. 9 to form a multiplicity of apertures 850. The non-apertured areas of the film substantially correspond to those areas where lands 124 of support members 123 contact the lowermost surface 665 of tubular forming member 622 during processing. FIG. 13 is a further enlarged view of the film sample shown in FIG. 11, said view being shown approximately sixteen times actual size for clarity.

Figure 10:
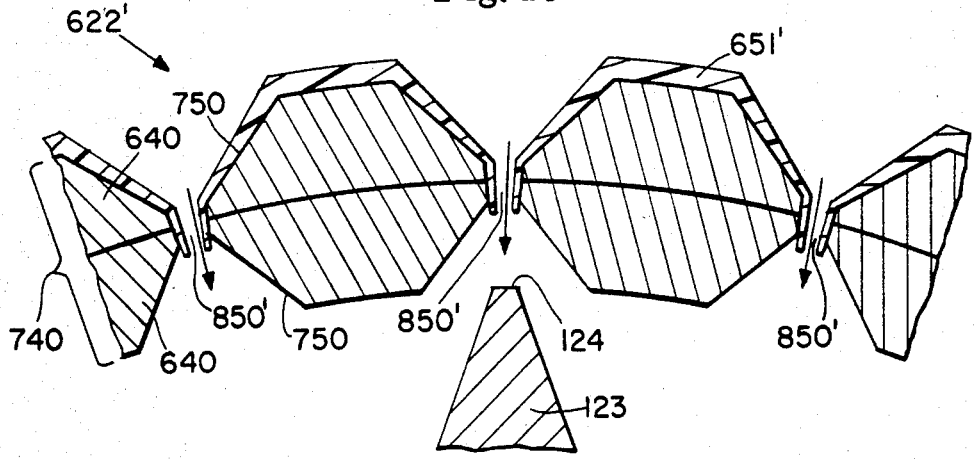
FIG. 10 is an enlarged, simplified cross-sectional segment of a two layer laminate forming structure of the present invention applied to a cylindrical cage of the type generally shown in FIGS. 1-3.

FIG. 10 illustrates a two layer embodiment of the present invention used to eliminate the problem created by the presence of lands 124 on support members 123, and at the same time ensure that fluid flow through the forming structure is not obstructed. Two laminar layers 640 employing patterns of non-straight walled apertures are bonded to one another at their points of interface to provide a laminate forming structure 740 which is thereafter formed into a tubular member 622' of the present invention. By placing the laminar layers 640 adjacent one another so that the cross-sectional area of each capillary network formed by the corresponding apertures in each layer reaches a minimum intermediate the outermost and innermost surfaces of the tubular member 622'; an increasing cross-sectional area is provided in the direction of the innermost surface of the member. This produces a continuous pattern of apertures 850' in film 651' in a manner generally similar to that of the embodiments disclosed in FIGS. 7 and 8.

Figure 11:
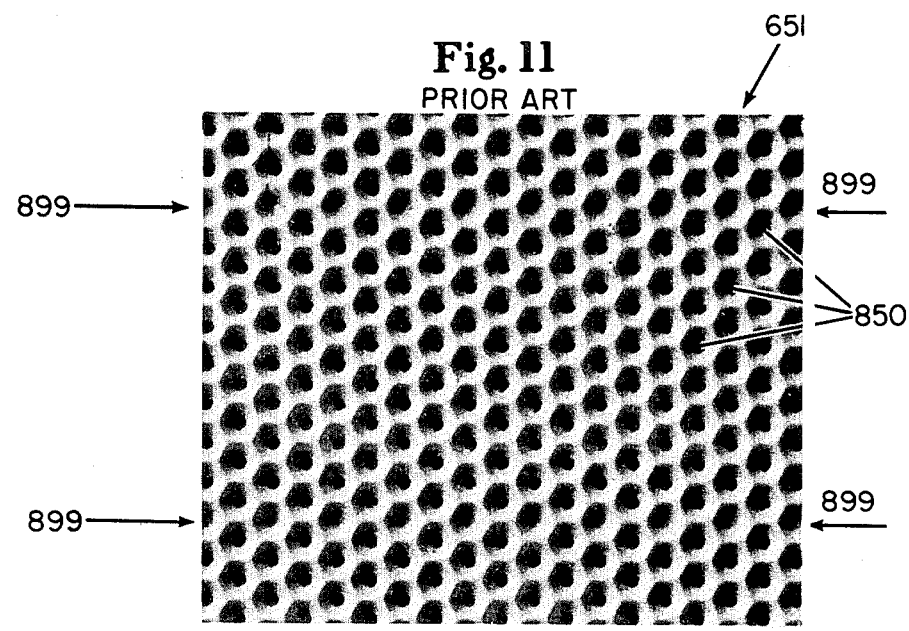
FIG. 11 is a plan view photograph enlarged approximately seven times actual size of a plastic film which has been debossed and apertured on a structure of the type generally shown in FIG. 9.
Figure 12:
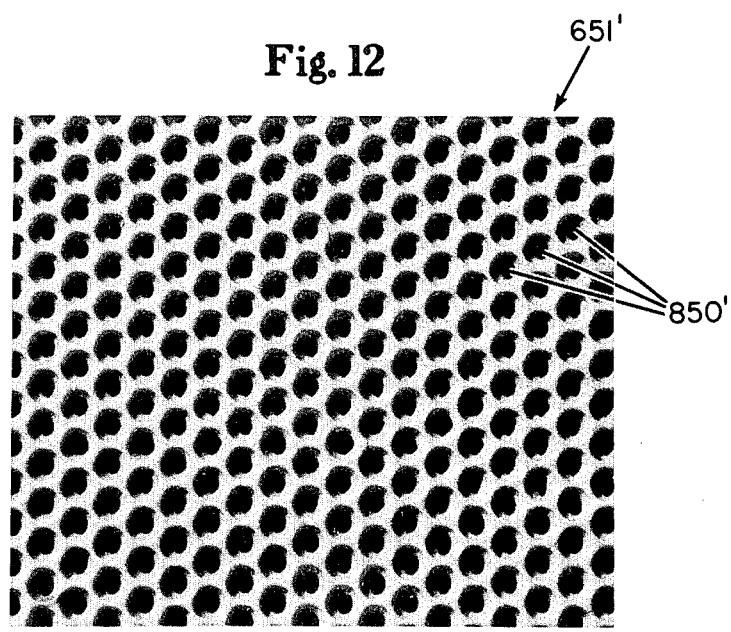
FIG. 12 is a plan view photograph enlarged approximately seven times actual size of a plastic film debossed and apertured on a structure of the type generally shown in FIG. 10.
Figure 14:
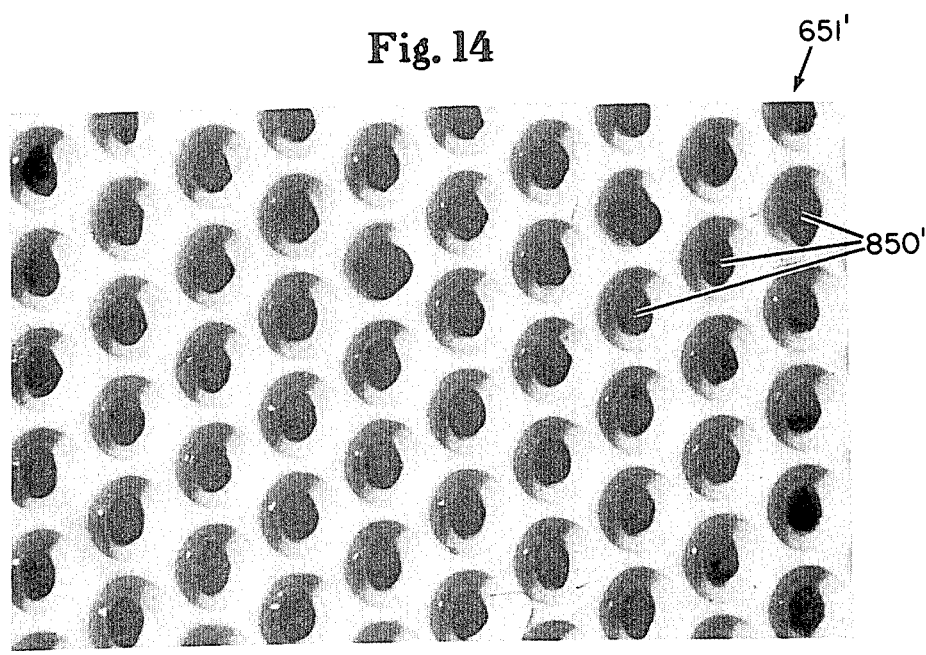
FIG. 14 is a further enlarged plan view photograph of the same film shown in FIG. 12, said film being shown approximately sixteen times actual size.

FIG. 12 is a plan view photograph generally similar to that of FIG. 11, enlarged approximately seven times actual size, but illustrating a plastic web 651' debossed and uniformly perforated on a forming structure of the type generally shown in FIG. 10. The tubular member 622' was utilized on the same cylindrical cage 120 employed with tubular member 622, and the processing conditions were similar. The benefit provided by the present invention is apparent from FIG. 12 in that the location of lands 124 on support members 123 during processing cannot be detected. Unlike the embodiment of FIGS. 11 and 13, uniform perforating of the film is provided at all locations. FIG. 14 is a further enlarged view of the film sample shown in FIG. 12, said view being shown approximately sixteen times actual size for clarity.

While particular embodiments of the present invention have been illustrated and described, it will be obvious to those skilled in the art that various changes and modifications can be made without departing from the spirit and scope of the invention. For example, the center lines of the coinciding apertures in the various laminae may be non-concentrically aligned with one another, forming structures of the present invention may be integrally formed utilizing machining rather than laminating techniques, the capillary networks employed in forming structures of the present invention may be regularly or irregularly shaped, their cross-sections may be uniform or nonuniform prior to reaching the point of expansion in the direction of the innermost surface of the tubular forming structure, they may be subdivided or non-subdivided, and the like. It is intended to cover in the appended claims all such modifications that are within the scope of this invention.

What is claimed is:

1. A forming cylinder for imparting an uninterrupted, uniformly apertured, fine scale three-dimensional pattern to a heated plastic film subjected to a fluid pressure differential while in contact with its surface, said cylinder comprising a tubular shaped structure exhibiting a three-dimensional continuum of capillary networks about its periphery, each of said capillary networks placing the outermost and innermost surfaces of said tubular member in exclusive fluid communication with one another, each of said capillary networks having an overall length greater than the maximum depth to which said film is drawn when subjected to said fluid pressure differential, each of said capillary networks also having a cross-sectional area which varies in size intermediate said outermost and innermost surfaces, said cross-sectional area reaching a minimum at a point intermediate said outermost and innermost surfaces and thereafter increasing in the direction of the innermost surface of said tubular member, said tubular member being supported at its innermost surface by a multiplicity of support members, each of said support members having a land which contacts the innermost surface of said tubular member, the width of said lands being insufficient to completely obstruct said capillary networks at their points of contact with the innermost surface of said tubular structure, said forming cylinder further including means for securing said multiplicity of support members in fixed relation to one another.

2. The forming cylinder of claim 1, wherein said tubular structure exhibits substantial continuity of said three-dimensional continuum of capillary networks about its entire periphery.

3. The forming cylinder of claim 1, wherein said multiplicity of support members are radially oriented with respect to one another.

4. The forming cylinder of claim 3, wherein said radially oriented support members are substantially uniformly spaced with respect to one another.

5. The forming cylinder of claim 1, wherein said capillary networks exhibit a substantially circular cross-section.

6. The forming cylinder of claim 1, wherein said capillary networks exhibit an irregular cross-section.

7. The forming cylinder of claim 6, wherein said capillary networks placing said outermost and said innermost surfaces of said tubular shaped structure in exclusive fluid communication with one another are subdivided intermediate said outermost and said innermost surfaces.

8. A forming cylinder for imparting an uninterrupted, uniformly apertured, fine scale three-dimensional pattern to a heated plastic film subjected to a fluid pressure differential while in contact with its surface, said cylinder comprising a tubular shaped laminate structure formed from a multiplicity of laminar sheets bonded to one another at their points of contact, each of said sheets having a substantially continuous pattern of apertures therein, said apertures in each of said sheets being concentrically aligned with the corresponding apertures in the balance of said sheets, said apertures in at least one of said laminar sheets being dissimilar in size from the corresponding apertures in another of said sheets, said corresponding apertures in said sheets thereby forming a three-dimensional continuum of capillary networks, each of said capillary networks placing the outermost and innermost surfaces of said tubular member in exclusive fluid communication with one another, each of said capillary networks having an overall length greater than the maximum depth to which said film is drawn when subjected to said fluid pressure differential, each of said capillary networks also having a cross-sectional area which varies in size intermediate said outermost and innermost surfaces, said cross-sectional area reaching a minimum at a point located intermediate said outermost and innermost surfaces and thereafter increasing in the direction of the innermost surface of said tubular member, said tubular member being supported at its innermost surface by a multiplicity of support members, each of said support members having a land which contacts the innermost surface of said tubular member, the width of said lands being insufficient to completely obstruct said capillary networks at their points of contact with the innermost surface of said tubular structure, said forming cylinder further including means for securing said multiplicity of support members in fixed relation to one another.

9. The forming cylinder of claim 8, wherein said tubular laminate structure exhibits substantial continuity of said three-dimensional continuum of capillary networks about its entire periphery.

10. The forming cylinder of claim 8, wherein said multiplicity of support members are radially oriented with respect to one another.

11. The forming cylinder of claim 10, wherein said radially oriented support members are substantially uniformly spaced with respect to one another.

12. The forming cylinder of claim 8, wherein said apertures in said substantially continuous patterns of concentrically aligned apertures are substantially circular in shape.

13. The forming cylinder of claim 8, wherein said apertures in said substantially continuous patterns of concentrically aligned apertures are formed by a multiplicity of intersecting fiber-like elements interconnected to one another at their ends.

* * * * *